United States Patent
Higuchi

(10) Patent No.: US 10,341,614 B2
(45) Date of Patent: Jul. 2, 2019

(54) BIOLOGICAL IMAGING DEVICE

(71) Applicant: NEC Corporation, Minato-ku, Tokyo (JP)

(72) Inventor: Teruyuki Higuchi, Tokyo (JP)

(73) Assignee: NEC CORPORATION, Tokyo (JP)

(*) Notice: Subject to any disclaimer, the term of this patent is extended or adjusted under 35 U.S.C. 154(b) by 0 days.

(21) Appl. No.: 16/123,078

(22) Filed: Sep. 6, 2018

(65) Prior Publication Data

US 2019/0007654 A1    Jan. 3, 2019

Related U.S. Application Data

(63) Continuation of application No. 15/995,257, filed on Jun. 1, 2018, now Pat. No. 10,205,912, which is a (Continued)

(30) Foreign Application Priority Data

May 19, 2010    (JP) ................... 2010-115362

(51) Int. Cl.
*G01B 11/00*    (2006.01)
*H04N 7/18*    (2006.01)
(Continued)

(52) U.S. Cl.
CPC ............ *H04N 7/18* (2013.01); *A61B 5/117* (2013.01); *A61B 5/1171* (2016.02); (Continued)

(58) Field of Classification Search
CPC .... G01B 11/00; G01B 11/24; G01N 2333/47; G01N 2333/705; G01N 2333/70546; (Continued)

(56) References Cited

U.S. PATENT DOCUMENTS 5,146,102 A * 9/1992 Higuchi .............. A61B 5/1172
                                              250/227.11
8,300,903 B2  10/2012 Higuchi
(Continued)

FOREIGN PATENT DOCUMENTS

CN     101526993 A    9/2009
CN     101536908 A    9/2009
(Continued)

OTHER PUBLICATIONS

The international search report for PCT/JP2011/061577 dated Jun. 21, 2011.
(Continued)

*Primary Examiner* — Michael P Stafira

(57) ABSTRACT

A biological imaging device includes an emitting unit that emits parallel light to a first part of a finger. The device includes an imaging unit that images the first part and a second part connected to the first part. The first part is a fingerprint part between a distal interphalangeal joint and a fingertip, and the second part is a part between a proximal interphalangeal joint and the distal interphalangeal joint. The device includes a finger root guide on which a root of the finger is placed.

2 Claims, 9 Drawing Sheets

Related U.S. Application Data continuation of application No. 15/801,544, filed on Nov. 2, 2017, now Pat. No. 10,003,771, which is a continuation of application No. 13/698,705, filed as application No. PCT/JP2011/061577 on May 19, 2011, now Pat. No. 9,826,198.

(51) Int. Cl.

| | | |
|---|---|---|
| *A61B 5/1171* | (2016.01) | |
| *A61B 5/117* | (2016.01) | |
| *A61B 5/1172* | (2016.01) | |
| *G06K 9/00* | (2006.01) | |
| *A61B 5/00* | (2006.01) | |

(52) U.S. Cl.
CPC ........ *A61B 5/1172* (2013.01); *G06K 9/00033* (2013.01); *G06K 9/00919* (2013.01); *H05K 999/99* (2013.01); *A61B 5/489* (2013.01); *A61B 5/6826* (2013.01); *G01B 11/00* (2013.01); *G06K 2009/00932* (2013.01)

(58) Field of Classification Search
CPC ..... G01N 2333/8121; G01N 2333/902; G01N 2333/914; G01N 2333/948; G01N 2333/9643; G01N 23/02; G01N 23/046; G01N 2500/00; G01N 2800/2814; G01N 2800/2821; G01N 2800/50; G01N 2800/52; G01N 2800/56; G01N 33/6896
See application file for complete search history.

(56) References Cited

U.S. PATENT DOCUMENTS

| | | |
|---|---|---|
| 8,339,486 B2 | 12/2012 | Nakashiba |
| 2002/0028004 A1 | 3/2002 | Miura et al. |
| 2005/0205667 A1 | 9/2005 | Rowe |
| 2006/0072796 A1 | 4/2006 | Sano et al. |
| 2006/0078170 A1 | 4/2006 | Kamata et al. |
| 2007/0217663 A1 | 9/2007 | Iizuka |
| 2007/0253607 A1 | 11/2007 | Higuchi |
| 2007/0285541 A1 | 12/2007 | Nakashiba |
| 2008/0002861 A1 | 1/2008 | Yano et al. |
| 2008/0075330 A1 | 3/2008 | Matsumura et al. |
| 2008/0107309 A1 | 5/2008 | Cerni |
| 2008/0117410 A1 | 5/2008 | Nagasaka et al. |
| 2008/0152195 A1 | 6/2008 | Nagasaka et al. |
| 2008/0175444 A1 | 7/2008 | Maro et al. |
| 2008/0226136 A1 | 9/2008 | Takaku et al. |
| 2008/0310690 A1 | 12/2008 | Higuchi |
| 2008/0317293 A1 | 12/2008 | Sakurai et al. |
| 2009/0110249 A1* | 4/2009 | Miura ................ G06K 9/00006 382/124 |
| 2009/0185726 A1* | 7/2009 | Higuchi ............. G06K 9/00033 382/124 |
| 2009/0304237 A1 | 12/2009 | Yoshikawa et al. |
| 2010/0046807 A1 | 2/2010 | Sato |
| 2010/0245556 A1* | 9/2010 | Kanda ................ G06K 9/00046 348/77 |
| 2014/0023249 A1 | 1/2014 | Higuchi |

FOREIGN PATENT DOCUMENTS

| | | |
|---|---|---|
| JP | 2004-234040 A | 8/2004 |
| JP | 2004-265269 A | 9/2004 |
| JP | 2007-213427 A | 8/2007 |
| JP | 2007-323389 A | 12/2007 |
| JP | 2008-310468 A | 12/2008 |
| JP | 2009-054095 A | 3/2009 |
| JP | 2009-069981 A | 4/2009 |
| JP | 2009-175810 A | 8/2009 |
| JP | 2010-049664 A | 3/2010 |

OTHER PUBLICATIONS

Chinese Office Action for CN Application No. 201180024826.6 dated Nov. 3, 2014 with English Translation.
Japanese Office Action for JP Application No. 2010-115362 dated Dec. 17, 2014 with English Translation.
Japanese Office Action for JP Application No. 2015-200406 dated Sep. 28, 2016 with English Translation.
Wenming Yang et al., "Personal Authentication Using Finger Vein Pattern and Finger-Dorsa Texture Fusion", Proceedings of the 17th ACM International Conference on Multimedia (MM '09), ACM, Beijing, China, Oct. 19, 2009, XP058271550, pp. 905-908.
Naoto Miura et al., "Extraction of Finger-Vein Patterns Using Maximum Curvature Points in Image Profiles", MVA2005 IAPR Conference on Machine Vision Applications, May 16-18, 2005, Tsukuba Science City, Japan, pp. 347-350.
Jinfeng Yang et al., "Finger-Vein Recognition Based on a Bank of Gabor Filters", Sep. 23, 2009, Lecture Notes in Computer Science, Springer, DE, XP019141356, pp. 374-383.
Extended European Search Report for EP Application No. EP11783631.2 dated Apr. 6, 2017.
U.S. Office Action for U.S. Appl. No. 15/995,257 dated Oct. 3, 2018.
U.S. Office Action for U.S. Appl. No. 15/801,544 dated Mar. 1, 2018.

* cited by examiner

BLOOD VESSEL

BIOLOGICAL IMAGING DEVICE

REFERENCE TO RELATED APPLICATION

This present application is a Continuation Application of Ser. No. 15/995,257 filed on Jun. 1, 2018, which is a Continuation Application of Ser. No. 15/801,544 filed on Nov. 2, 2017, which is a Continuation Application of Ser. No. 13/698,705 filed on Nov. 19, 2012, U.S. Pat. No. 9,826,198 issued on Nov. 21, 2017, which is a National Stage Entry of International Application PCT/JP2011/061577 filed on May 19, 2011, which claims the benefit of priority from Japanese Patent Application 2010-115362, filed on May 19, 2010, the disclosures of all of which are incorporated in their entirety by reference herein.

TECHNICAL FIELD

The present invention relates to a biological imaging device and a biological imaging method.

BACKGROUND ART

The biological authentication technology of authenticating a person using an image of a finger is known as a technique of collating a pattern of epidermis such as a fingerprint, and a pattern of a blood vessel with pre-registered information.

One example of such a biological authentication technology is described in Patent literature 1.

FIG. 10 is a block diagram of the invention of the Patent literature 1.

In the invention of the Patent literature 1, when personal identification utilizing a blood vessel pattern of the finger is performed, the finger, being a target of authentication, is placed between infrared light sources 310 and 320 and an infrared-transparent filter 330. When a driving circuit 360 is driven by a microcomputer 370 to turn on the infrared light source 310, the blood vessel pattern is imaged onto an image sensor 350 via a lens 340 because infrared light is absorbed by hemoglobin of the blood. Additionally, the infrared-transparent filter 330 has a feature of blocking visual light that becomes noise at the moment of obtaining the blood vessel pattern, and allowing only the infrared light in which the blood vessel pattern is included to be transmitted. On the other hand, when personal identification utilizing a fingerprint pattern is performed, the finger, being a target of authentication, is placed at a position identical to the position in which the personal identification utilizing the blood vessel pattern of the finger is performed. When the infrared light source 310 is kept being turned off, the surface of the finger is imaged onto the image sensor 350 via the lens 340. The blood vessel pattern or the fingerprint pattern imaged by the image sensor 350, which is subjected to a photoelectric conversion and is converted into an electric signal, is inputted into the microcomputer 370. Additionally, the infrared light source 320 is turned on in order to obtain brightness sufficient for obtaining the fingerprint pattern.

In such a manner, the invention of the Patent literature 1 is the personal authentication device of separately imaging the blood vessel and the fingerprint with a single imaging means by switching the light source for emitting light.

Further, the biological image input device including an imaging unit that makes infrared light incident into the inside of the finger and takes the fingerprint image and the blood vessel image by use of its scattered light is described in Patent literature 2. The above biological image input device, which includes a window material in which a fiber plate and a transparent plate of which thickness is thicker than that of the fiber plate are arranged in parallel on a light incident side of the imaging unit, is configured to image the fingerprint through the fiber plate side of the window material and to image the blood vessel through the transparent plate side of the window material therewith in such a manner that the fingerprint of a fingertip part is contacted with the fiber plate side of the window material.

CITATION LIST

Patent Literature

PTL 1: JP-P2004-234040A
PTL 2: JP-P2009-69981A

SUMMARY OF INVENTION

Technical Problem

The inventions disclosed in the above-mentioned patent literatures, however, have the following problems.

At first, the invention of the patent literature 1 can obtain the blood vessel image having an excellent contrast owing to a reflected light technique; however it requires a big device because the light source needs to be placed on the finger or in the side of the finger. Further, there is a problem that it is difficult to place the finger due to disturbance by the light source and hence, maneuverability deteriorates.

In addition, the invention of the patent literature 1 has a problem that it takes much time to obtain information for authentication because the fingerprint image and the blood vessel image need to be separately taken by switching the light source, and the fingerprint image and the blood vessel image cannot be taken at a time.

Further, the invention of the patent literature 2, which is configured to read out the fingerprint and the blood vessel by contacting the finger with the plate or the transparent plate, has a problem that it is difficult to obtain the blood vessel image because the blood vessel is oppressed and thus, the blood runs away.

Thereupon, the present invention has been accomplished in consideration of the above-mentioned problems, and an object of the present invention is to provide the biological imaging device capable of simultaneously taking the images of the blood vessel of the finger and the fingerprint without switching the light source, and the biological imaging method thereof.

Means for Solving Problem

The present invention for solving the above-mentioned problems is a biological imaging device including an emitting unit that emits parallel light to a first part of a living body, and an imaging unit that images the aforementioned first part and a second part connected to the aforementioned first part.

The present invention for solving the above-mentioned problems is a biological imaging method of emitting parallel light to a first part of a living body, and simultaneously imaging the aforementioned first part and a second part connected to the aforementioned first part.

Advantageous Effect of Invention

The present invention makes it possible to simultaneously image the blood vessel of the finger and the fingerprint without switching the light source.

DESCRIPTION OF EMBODIMENTS

The exemplary embodiment of the present invention will be explained.

In the exemplary embodiment of the present invention, an example of applying the biological imaging device of the present invention to the personal authentication device in such a manner that the living bodies, for example, the fingerprint of the finger and the blood vessel of human being are imaged is shown.

Figure 1:
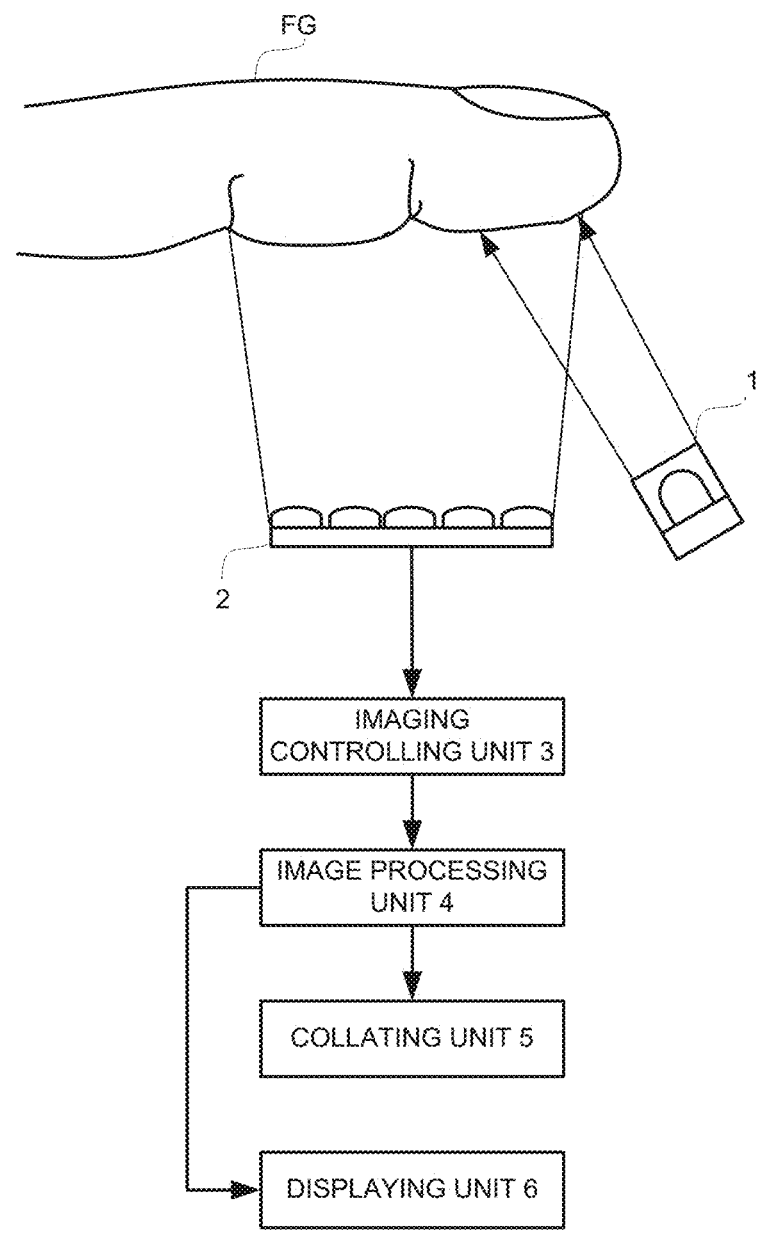
FIG. 1 is a block diagram of the personal authentication device in this exemplary embodiment.

FIG. 1 is a block diagram of the personal authentication device in this exemplary embodiment. As shown in FIG. 1, the personal authentication device in first exemplary embodiment includes a spotlight generating light source 1, an imaging unit 2, an imaging controlling unit 3, an image processing unit 4, a collating unit 5, and a displaying unit 6.

The spotlight generating light source 1, which is installed at a position in which the spotlight generating light source 1 is not contacted with a finger FG, emits parallel light to an entirety of the fingerprint part between a distal interphalangeal joint (first knuckle joint) of the finger FG and the fingertip in a spot manner for the fingerprint part at almost uniform luminance. Herein, the so-called parallel light signifies light that is uniformly applied to the fingerprint part (the surface of the fingerprint part) at almost identical angle. Further, in order to image the fingerprint, being concave and convex areas of the epidermis of the finger FG, the spotlight generating light source 1 preferably emits light from one direction because it is desired that shadow due to the concave and convex areas of the epidermis can be formed as much as possible.

The spotlight of the spotlight generating light source 1 preferably includes a wavelength component, being a wavelength of 1000 to 600 nm or so, known to be easily transmitted through a body structure except bones of human being, and the spotlight generating light source is configured of, for example, halogen lamps, xenon lamps and lenses, LEDs having a luminous feature within the corresponding wavelength to which lenses belong, or the like.

The imaging unit 2 is configured of an image sensor such as CCD and CMOS, a control system, and a lens optical system for imaging the fingerprint and the blood vessel of the finger onto the image sensor, and the like. Herein, the imaging unit 2 images the fingerprint of the fingerprint part between the distal interphalangeal joint (first knuckle joint) of the finger FG and the fingertip with the reflected light by the emitted light coming from the spotlight generating light source 1 to the fingerprint part between the distal interphalangeal joint (first knuckle joint) of the finger FG and the fingertip taken as main light, and takes the blood vessel image by use of the scattered light that leaks out (is radiated) from the epidermis between the distal interphalangeal joint (first knuckle joint) and a proximal interphalangeal joint (second knuckle joint) as a result of light emitted from the spotlight generating light source 1 to the fingerprint part being scattered inside the finger FG and being propagated. Additionally, the fingerprint image and the blood vessel image are simultaneously taken by the imaging unit 2. Additionally, the imaging unit 2 is installed at a position in which the imaging unit 2 is not contacted with the finger FG similarly to the spotlight generating light source 1.

The imaging controlling unit 3 controls the imaging of the imaging unit 2, converts the signal of the imaging unit 2 into data, and sends the fingerprint image and the blood vessel image to the image processing unit 4.

The image processing unit 4 extracts a center of the fingerprint from the image data of the fingerprint acquired from the imaging controlling unit 3, and measures a shift of the center from an outer shape of the finger FG. And, the image processing unit 4 detects a rotational quantity of the finger, displays correct position modification information of the finger on the displaying unit 6 with the above rotational quantity, and urges an authenticatee who receives the authentication to perform a positional modification so that the finger is correctly placed. In addition, the image processing unit 4 extracts image characteristics of the fingerprint and the finger blood vessel from the data of the image taken by the imaging unit 2 after the position of the finger FG has been correctly modified, and outputs the extracted image characteristic data to the collating unit 5.

The collating unit 5, which has the image characteristics of the fingerprint and the finger blood vessel of the authenticatee stored therein, collates the stored image characteristics of the fingerprint and the finger blood vessel of the authenticatee and the image characteristics of the fingerprint and the finger blood vessel coming from the image processing unit 4 with each other, and performs the authentication.

Additionally, the image processing unit 4 or the collating unit 5 may be configured to pre-stores a plurality of pieces of reference data (the image characteristics of the fingerprint and the finger blood vessel) by pre-rotating the finger of the authenticatee, to select the finger having a rotational quantity resembling the image characteristics of the fingerprint and the finger blood vessel extracted by the image processing unit 4, and to perform the collation with the image characteristics of the fingerprint and the finger blood vessel thereof.

Next, an operation of the imaging and the collation of the fingerprint and the blood vessel in the first exemplary embodiment will be explained.

Figure 2:
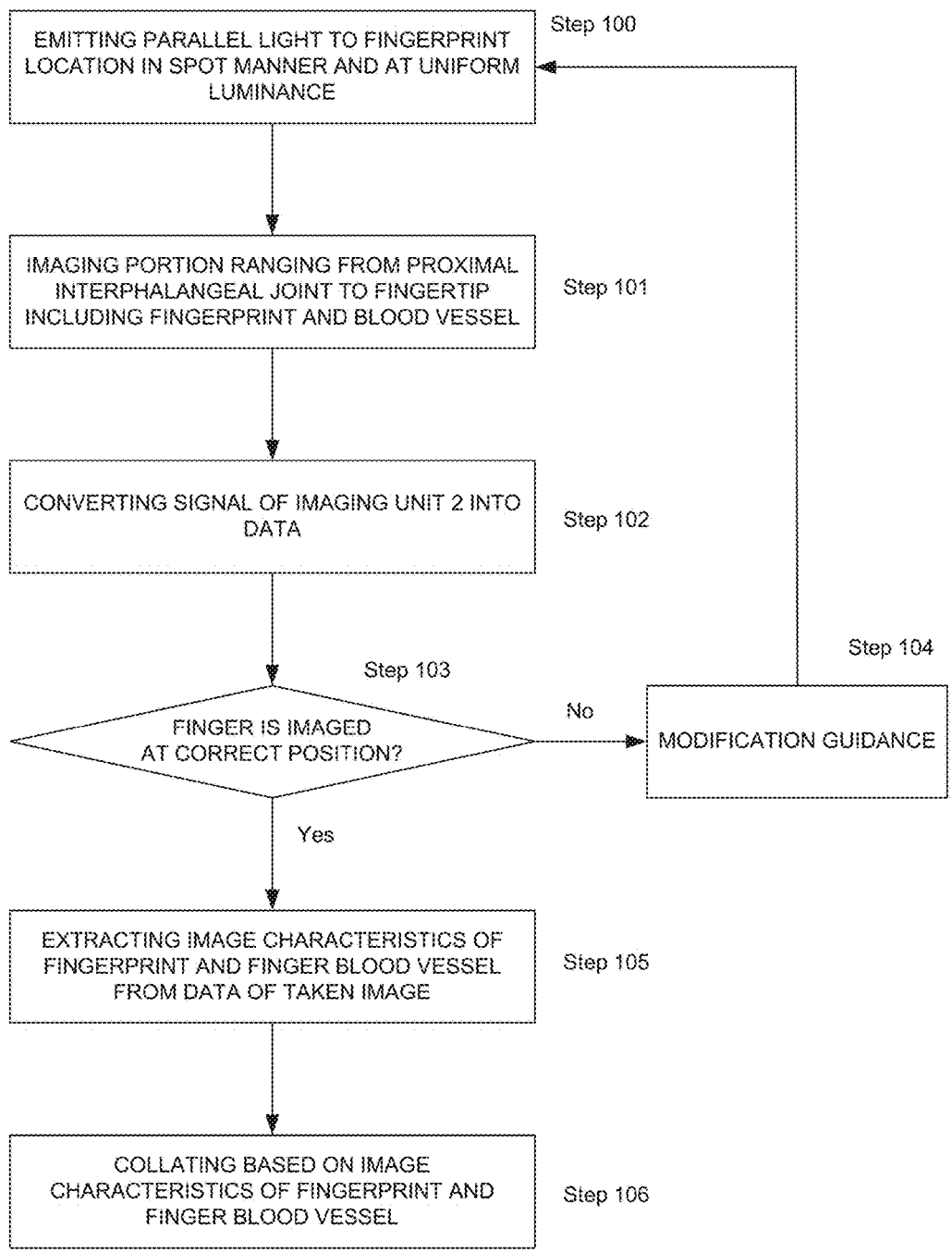
FIG. 2 is an operational flowchart of the imaging and the collation of the fingerprint and the blood vessel in a first exemplary embodiment.

FIG. 2 is an operational flowchart of the imaging and the collation of the fingerprint and the blood vessel in the first exemplary embodiment.

At first, the spotlight generating light source 1 emits parallel light to an entirety of the fingerprint part higher than the distal interphalangeal joint (first knuckle joint) of the finger FG in a spot manner at uniform luminance (Step 100).

The imaging unit 2 images the part ranging from the proximal interphalangeal joint (second knuckle joint) of the finger FG to the fingertip including the fingerprint and the blood vessel by the imaging controlling unit 3 (Step 101). Herein, the fingerprint part between the distal interphalangeal joint (first knuckle joint) of the finger FG and the fingertip is imaged with the reflected light by the emitted light taken as main light. On the other hand, comparatively thick blood vessels exist between the distal interphalangeal joint (first knuckle joint) of the finger FG and the proximal interphalangeal joint (second knuckle joint), and just under the skin in the neighborhood of the joint. Light emitted to the fingerprint part by the spotlight generating light source 1 is scattered inside the finger, is propagated inside the finger, and is radiated from the epidermis, and the blood vessel image is taken in this part. Additionally, the fingerprint image and the blood vessel image are simultaneously taken.

The imaging controlling unit 3 converts the signal of the imaging unit 2 into data, and outputs the fingerprint image and the blood vessel image to the image processing unit 4 (Step 102).

The image processing unit 4 extracts a center of the fingerprint, and determines whether the finger FG of the authenticatee has been imaged at a position suitable for the collation by use of the rotational quantity of the finger (Step 103).

When the finger FG of the authenticatee is not placed at a position suitable for the collation, the image processing unit 4 urges the authenticatee to perform a positional modification so that the finger is correctly placed by making a display on the displaying unit 6. For example, the image processing unit 4 pre-registers the guidance images to be displayed to the authenticatee in plural number such as "do not lean the finger", "lean the finger to the right", "lean the finger to the left", and the like, and displays the appropriate guidance image depending on the rotational quantity of the finger (Step 104).

The image processing unit 4 extracts the image characteristics of the fingerprint and the finger blood vessel from the data of the image taken by the imaging unit 2 after the position of the finger FG has been correctly modified, and outputs the extracted image characteristic data to the collating unit 5 (Step 105).

The collating unit 5 performs the collation based on the image characteristics of the fingerprint and the finger blood vessel coming from the image processing unit 4 (Step 106).

As explained above, the first exemplary embodiment exhibits an effect described below.

The effect of the first exemplary embodiment lies in a point of being able to perform a collating process (personal authentication) with a simplified structure for a short time because the blood vessel image by use of the scattered light that leaks out (is radiated) from the epidermis between the distal interphalangeal joint (first knuckle joint) and the proximal interphalangeal joint (second knuckle joint) as a result of the parallel light being emitted to the fingerprint part of the finger in a spot manner, being scattered inside the finger from the fingerprint part and being propagated, and the fingerprint image by use of the parallel light emitted to the fingerprint part of the finger in a spot manner are simultaneously taken by one imaging unit.

Further, the parallel light to be emitted to the fingerprint part in a spot manner enables the shadow due to the concave and convex areas of the fingerprint to be easily formed, and the scattered light enables the fingerprint image having an excellent contrast to be obtained.

In addition, the effect of the first exemplary embodiment lies in a point of being able to perform a personal authentication with a higher precision because the fingerprint center is obtained from the simultaneously taken fingerprint images, an inclination (rotational) quantity of the finger is detected therewith, the guidance for urging the authenticatee to amend an inclination of the finger is shown to the authenticatee, and the re-imaging is performed or the collation with the reference data pre-registered by pre-rotating the finger is performed.

EXAMPLE 1

Next, a specific example 1 corresponding to the first exemplary embodiment will be explained.

Figure 3:
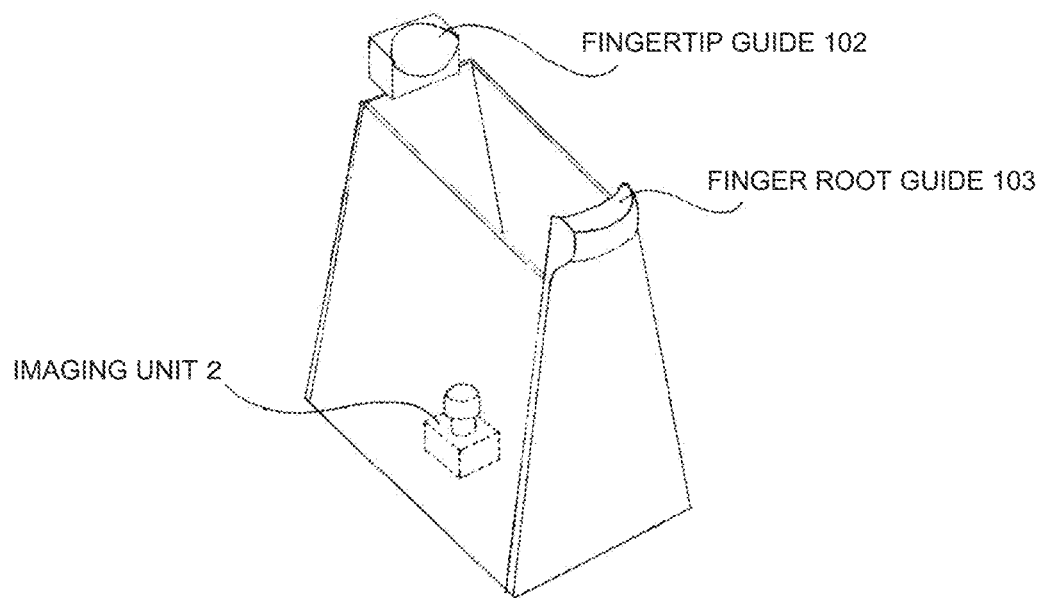
FIG. 3 is a perspective view of the biological imaging device of an example 1.

FIG. 3 is a perspective view of the biological imaging device of the example 1.

The biological imaging device of the example 1, as shown in FIG. 3, includes the imaging unit 2 mounted inside the biological imaging device, and assumes a configuration in which a fingertip guide 102 for guiding, for this imaging unit 2, the imaging region of the fingerprint of the finger and finger blood vessel pattern to a position suitable for the photography, and a finger root guide 103 are mounted on the upper side of the imaging unit 2. Additionally, in order to prevent at least the fingerprint part, being a target of the imaging, and the epidermis part between the distal interphalangeal joint (first knuckle joint) and the proximal interphalangeal joint (second knuckle joint), out of the finger of the user (authenticatee), from being oppressed, namely, from being contacted with any members, the portions corresponding to these parts are opened.

Herein, at the moment of photographing the finger, the finger of the user is guided to a position suitable for the imaging by the imaging unit 2 by placing a tip of the finger of the user (authenticatee) on the fingertip guide 102, and placing a root of the above finger (finger root portion) on the finger root guide 103.

Figure 4:
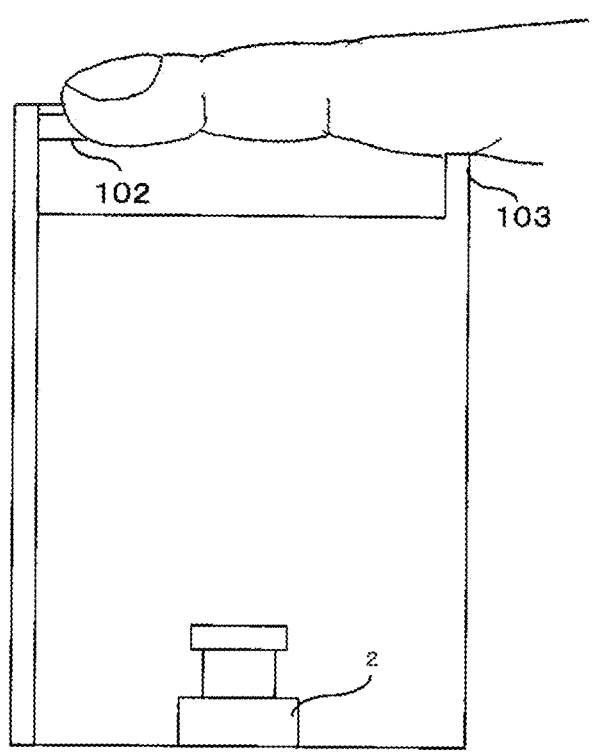
FIG. 4 is a view for explain the example 1.

With regard to the fingertip guide 102 and the finger root guide 103, when the fingerprint of the finger and the blood vessel pattern of the user are imaged by an imaging means 104, the photographing region of the finger, as shown in FIG. 4, is guided to a photographable position by placing the tip of the finger on the fingertip guide 102 and placing the root of the identical finger on the finger root guide 103.

Figure 5:
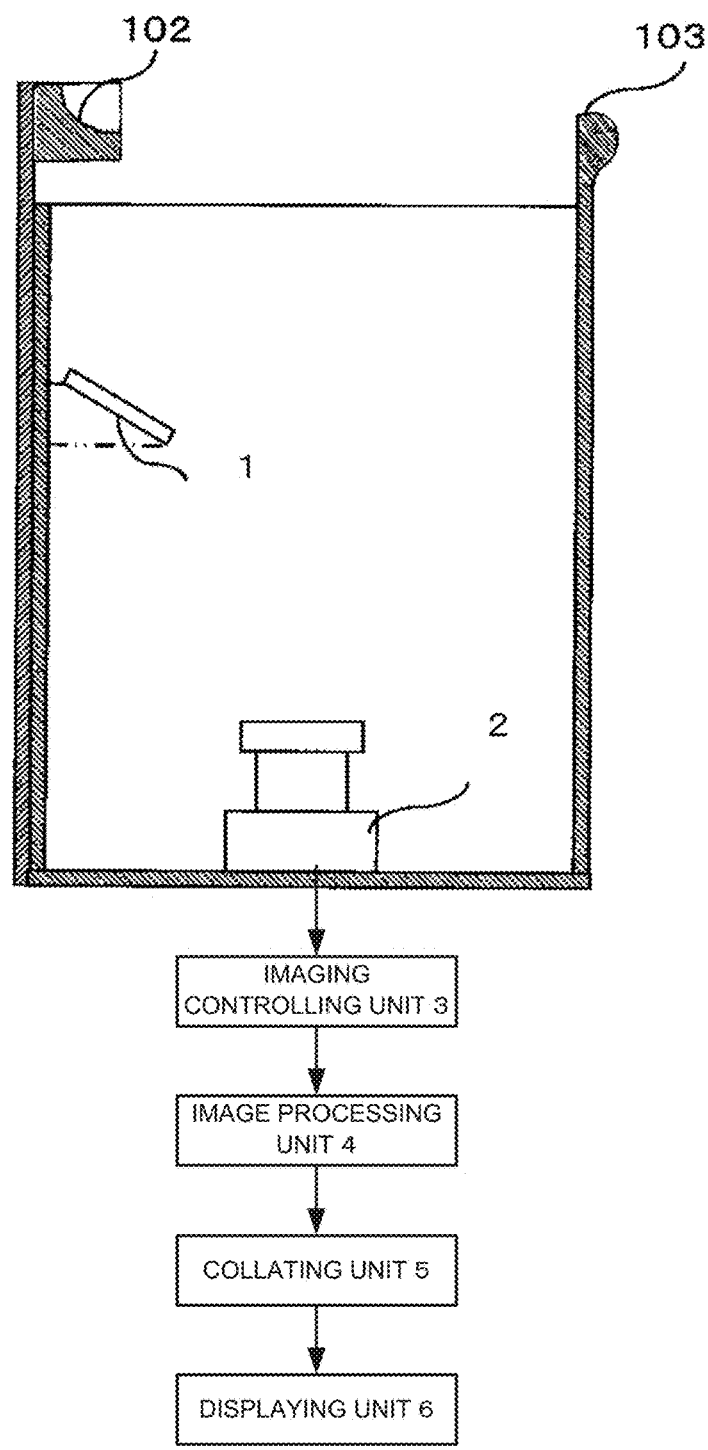
FIG. 5 is a longitudinal sectional view of the biological imaging device.

Herein, the longitudinal sectional view including the imaging unit 2 of the biological imaging device is shown in FIG. 5. Additionally, for a convenience for explanation, the imaging controlling unit 3, the image processing unit 4, the collating unit 5 and the displaying unit 6 mounted in the external are also listed.

The spotlight generating light source 1, as described above, is installed in a non-contact with the finger FG, and is mounted at a position in which the spotlight generating light source 1 can emit the parallel light to an entirety of the fingerprint part between the distal interphalangeal joint (first knuckle joint) of the finger and the fingertip of the user in a spot manner for the fingerprint part at almost uniform luminance from one direction.

Further, in the biological imaging device of the example 1, the portions corresponding to the fingerprint part and the part (the part in which the image of the finger blood vessel is taken) between the distal interphalangeal joint (first knuckle joint) and the proximal interphalangeal joint (second knuckle joint) are opened so that the part, being a target of the imaging of the finger of the user (authenticatee), that is, the fingerprint part and the part (the part in which finger blood vessel is imaged) between the distal interphalangeal joint (first knuckle joint) and the proximal interphalangeal joint (second knuckle joint) are kept in non-contact with anything so as to prevent the blood from running away due to the blood vessel being oppressed.

Figure 6:
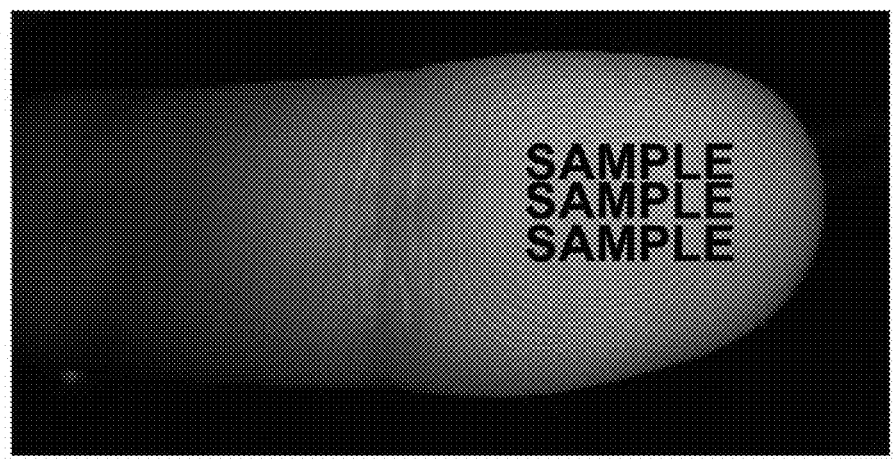
FIG. 6 is a view illustrating one example of the fingerprint image and the blood vessel image taken by the biological imaging device of the example 1.

One example of having imaged the fingerprint and the blood vessel pattern of the user (authenticatee) by the biological imaging device of the example 1 is shown in FIG. 6.

As shown in FIG. 6, it can be seen that by emitting the parallel light to the fingerprint part of the finger in a spot manner, the finger image by use of the reflected light reflected on the surface of the fingerprint part of the finger, and the blood vessel image by use of the radiated light that is radiated as a result of the above emitted light beings propagated inside the finger are simultaneously taken by one imaging unit.

Figure 7:
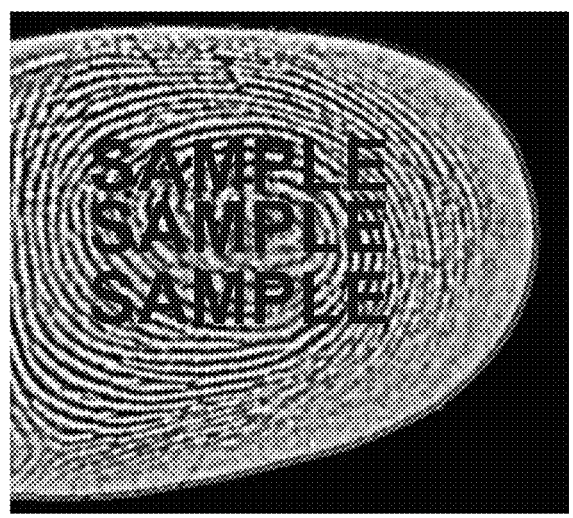
FIG. 7 is a view illustrating one example of having subjected the fingerprint image taken by the biological imaging device of the example 1 to an image process.
Figure 8:
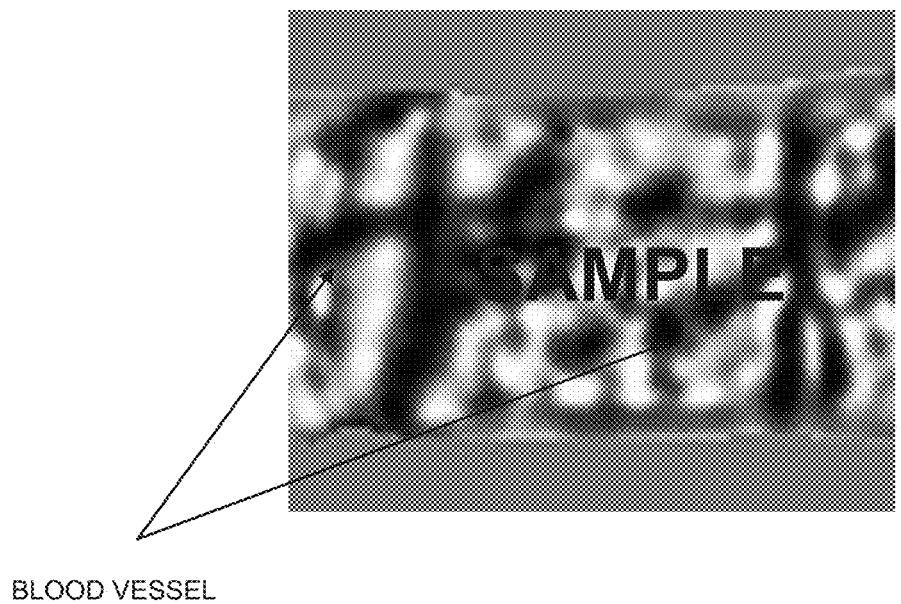
FIG. 8 is a view illustrating an image obtained by subjecting the blood vessel image taken by the biological imaging device of the example 1 to the image process.

Further, FIG. 7 and FIG. 8 are views illustrating the fingerprint image and the blood vessel image obtained by subjecting the biological taken image shown in FIG. 6 to the image processes such as nose removal, image emphasis by a frequency filter, and image emphasis by a gain adjustment, respectively.

As the fingerprint image subjected to the image processes shown in FIG. 7 indicates, it can be seen that the parallel light that is emitted to the fingerprint part in a spot manner enables the shadow to be easily formed due to the concave and convex areas of the fingerprint, and the scattered light enables the fingerprint image having an excellent contrast to be obtained. Further, as the blood vessel image subjected to the image processes shown in FIG. 8 indicates, it can be seen that the scattered light that leaks out (is radiated) from the epidermis between the distal interphalangeal joint (first knuckle joint) and the proximal interphalangeal joint (second knuckle joint) enables the image having a clear blood vessel pattern to be obtained.

Another exemplary embodiment of the present invention will be explained.

Figure 9:
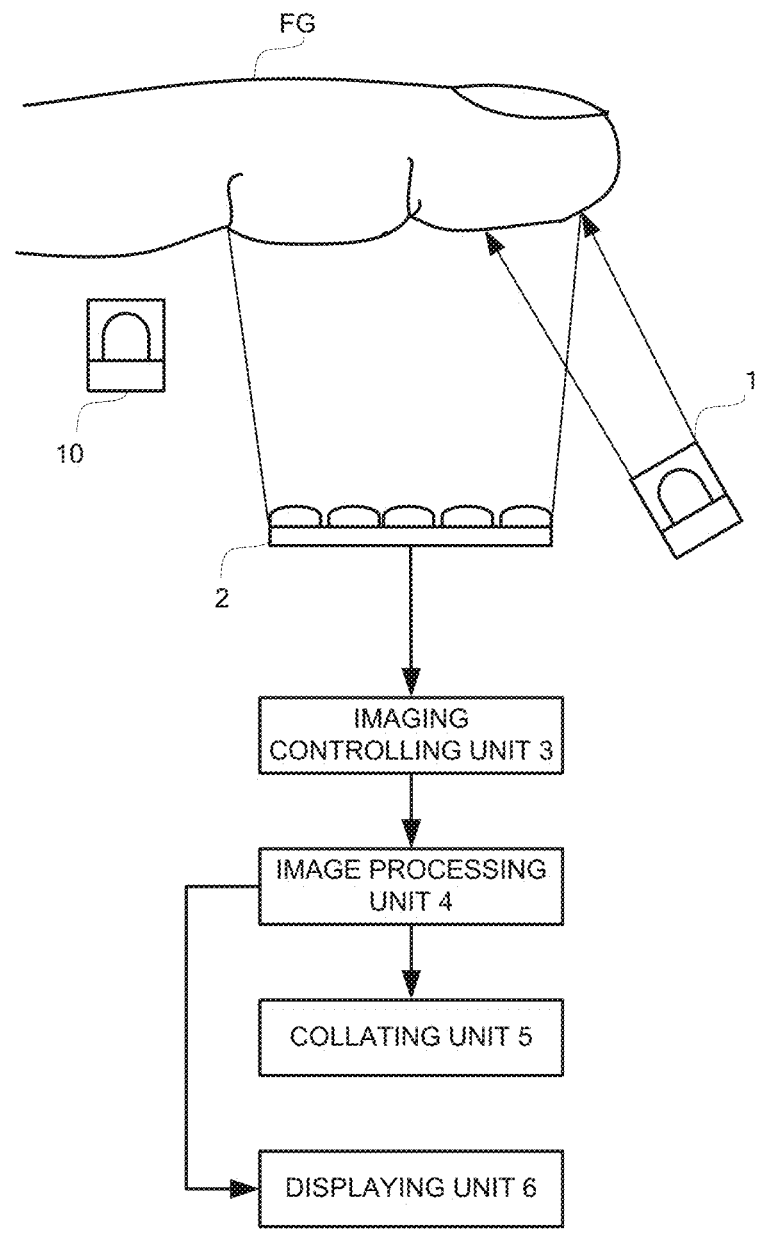
FIG. 9 is a block diagram of the personal authentication device in another exemplary embodiment.
Figure 10:
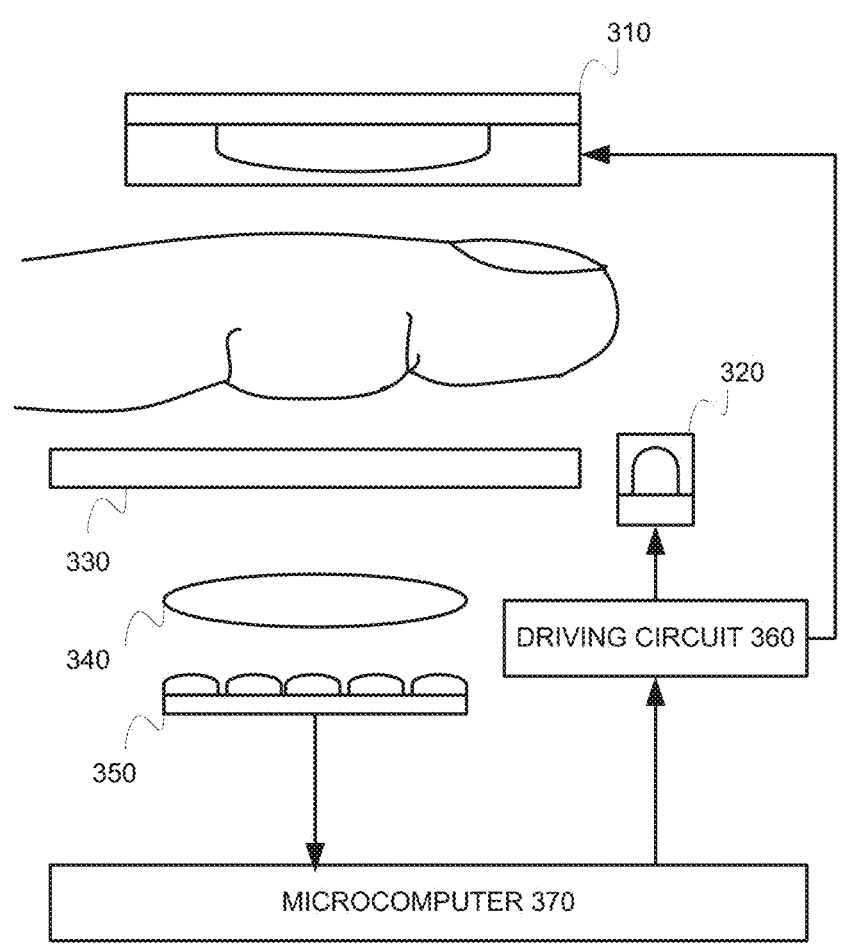
FIG. 10 is a view for explaining the technology related to the present invention.

A basic configuration of another exemplary embodiment of the present invention is identical to that of the above-described exemplary embodiment; however, the light source is furthermore contrived in order to image the more stable blood vessel. Its configuration is shown in FIG. 9.

Another exemplary embodiment is characterized in mounting an auxiliary light source 10 in addition to the components of the above-described exemplary embodiment. The auxiliary light source 10, which is installed in the neighborhood of the root side of the proximal interphalangeal joint (second knuckle joint) of the finger FG, emits light to the inside of the finger.

The scattered light can be observed between the first knuckle joint and the second knuckle joint only with the spotlight generating light source 1 located in the fingertip; however, there is a problem that the root side of the finger is darkened, and this auxiliary light source enables the situation to be improved.

Further, the content of the above-mentioned exemplary embodiments can be expressed as follows.

(Supplementary note 1) A biological imaging device, comprising:
an emitting unit that emits parallel light to a first part of a living body; and
an imaging unit that images said first part and a second part connected to said first part.

(Supplementary note 2) The biological imaging device according to Supplementary note 1:
wherein the first part is a fingerprint part between a distal interphalangeal joint and a fingertip; and
wherein the second part is a part between a proximal interphalangeal joint and the distal interphalangeal joint.

(Supplementary note 3) The biological imaging device according to Supplementary note 1 or Supplementary note 2, wherein said emitting unit emits light including a wavelength of 600 nm to 1000 nm.

(Supplementary note 4) The biological imaging device according to one of Supplementary note 1 to Supplementary note 3, wherein said first part and said second part are kept at a position in which they are not contacted with any members.

(Supplementary note 5) The biological imaging device according to one of Supplementary note 1 to Supplementary note 4, wherein said imaging unit images said first part and said second part with reflected light that has been emitted by said emitting unit and has been reflected on the surface of said first part, and radiated light that has been emitted by said emitting unit, has been propagated inside said second part, and has been radiated, respectively.

(Supplementary note 6) The biological imaging device according to one of Supplementary note 1 to Supplementary note 5, comprising a second emitting unit that emits light to a third part that exists continuously with said second part existing in a side opposite to that of said first part.

(Supplementary note 7) A biological imaging method, comprising:
emitting parallel light to a first part of a living body; and
simultaneously imaging said first part and a second part connected to said first part.

(Supplementary note 8) The biological imaging method according to Supplementary note 7:
wherein the first part is a fingerprint part between a distal interphalangeal joint and a fingertip; and
wherein the second part is a part between a proximal interphalangeal joint and the distal interphalangeal joint.

(Supplementary note 9) The biological imaging method according to Supplementary note 7 or Supplementary note 8, wherein a wavelength of said parallel light is 600 nm to 1000 nm.

(Supplementary note 10) The biological imaging method according to one of Supplementary note 7 to Supplementary note 9, wherein said first part and said second part are imagined at a position in which they are not contacted with any members.

(Supplementary note 11) The biological imaging method according to one of Supplementary note 7 to Supplementary note 11, comprising:
imaging said first part and said second part with reflected light that has been emitted by parallel light and has been reflected on the surface of said first part, and radiated light that has been emitted by parallel light, has been propagated inside said second part, and has been radiated, respectively.

(Supplementary note 12) The biological imaging method according to one of Supplementary note 7 to Supplementary note 11, comprising:

emitting light to a third part that exists continuously with said second part existing in a side opposite to that of said first part.

(Supplementary note 13) A biological imaging device, comprising:

holding means that hold a fingerprint part of a finger and a blood vessel part of said finger for keeping at a position in which they are not contacted with any members, an emitting unit is arranged below said hold finger, that emits parallel light to said fingerprint part and an imaging unit that images said fingerprint part and said blood vessel part;

wherein said fingerprint part is a part between a part between a distal interphalangeal joint of said finger and a fingertip of said finger and said blood vessel part is a part between a proximal interphalangeal joint of said finger and the distal interphalangeal joint of said finger.

(Supplementary note 14) The biological imaging device according to Supplementary note 13, wherein said emitting unit emits light including a wavelength of 600 nm to 1000 nm.

Above, although the present invention has been particularly described with reference to the preferred embodiments and examples, it should be readily apparent to those of ordinary skill in the art that the present invention is not always limited to the above-mentioned embodiments and examples, and changes and modifications in the form and details may be made without departing from the spirit and scope of the invention.

This application is based upon and claims the benefit of priority from Japanese patent application No. 2010-115362, filed on May 19, 2010, the disclosure of which is incorporated herein in its entirety by reference.

REFERENCE SIGNS LIST 1 spotlight generating light source
2 imaging unit
3 imaging controlling unit
4 image processing unit
5 collating unit
6 displaying unit

The invention claimed is:

1. A biological imaging device, comprising:
an emitting unit that emits parallel light to a first part of a finger;
an imaging unit that images the first part and a second part connected to the first part, wherein the first part is a fingerprint part between a distal interphalangeal joint and a fingertip and the second part is a part between a proximal interphalangeal joint and the distal interphalangeal joint; and
a finger root guide on which a root of the finger is placed
wherein the imaging unit captures blood vessel of the second part, the parallel light emitted by the light propagating inside the finger and radiated from the second part.

2. The biological imaging device according to claim 1, wherein
the first part is a part at least between a distal interphalangeal joint and a fingertip; and
the second part is a part between at least a proximal interphalangeal joint and the distal interphalangeal joint.

* * * * *